United States Patent
Clarke et al.

(10) Patent No.: US 12,083,267 B2
(45) Date of Patent: Sep. 10, 2024

(54) INHALER

(71) Applicant: VECTURA DELIVERY DEVICES LIMITED, Wiltshire (GB)

(72) Inventors: Roger Clarke, Cambridgeshire (GB); Andreas Meliniotis, Cambridgeshire (GB)

(73) Assignee: VECTURA DELIVERY DEVICES LIMITED (GB)

( * ) Notice: Subject to any disclaimer, the term of this patent is extended or adjusted under 35 U.S.C. 154(b) by 848 days.

(21) Appl. No.: 17/277,101

(22) PCT Filed: Sep. 18, 2019

(86) PCT No.: PCT/EP2019/074978
§ 371 (c)(1),
(2) Date: Mar. 17, 2021

(87) PCT Pub. No.: WO2020/064454
PCT Pub. Date: Apr. 2, 2020

(65) Prior Publication Data
US 2021/0369989 A1    Dec. 2, 2021

(30) Foreign Application Priority Data
Sep. 25, 2018  (EP) .................................... 18196709

(51) Int. Cl.
*A61M 15/00*        (2006.01)
(52) U.S. Cl.
CPC .... *A61M 15/0051* (2014.02); *A61M 15/0001* (2014.02); *A61M 2202/064* (2013.01)
(58) Field of Classification Search
CPC .......... A61M 15/0051; A61M 15/0001; A61M 15/0021; A61M 15/0026; A61M 15/0035;
(Continued)

(56) References Cited

U.S. PATENT DOCUMENTS 5,619,984 A * 4/1997 Hodson ............. A61M 15/0006
                                                    128/203.15
8,161,968 B2 * 4/2012 Augustyn ......... A61M 15/0025
                                                    128/203.15
(Continued)

FOREIGN PATENT DOCUMENTS

WO    WO 2013/175176 A1    11/2013

OTHER PUBLICATIONS

European Search Report from corresponding European Application No. 18196709.2, mailed Feb. 28, 2019.
(Continued)

*Primary Examiner* — Justine R Yu
*Assistant Examiner* — Matthew R Moon
(74) *Attorney, Agent, or Firm* — Davidson Kappel LLC

(57) ABSTRACT

An inhaler is provided, comprising a housing which contains a blister strip having a plurality of blisters which contain powdered medicament for inhalation; a mouthpiece mounted on the housing through which the medicament is inhaled by a user; an actuator; a blister piercing member; an indexing wheel for sequentially moving each blister into alignment with the blister piercing member when the user operates the actuator; an actuator gear, mounted for rotation about a first axis, which is driven by the actuator and which comprises an actuator gear element; and a drive gear for driving the indexing wheel, mounted for rotation about a second axis, which engages with the actuator gear element. The inhaler is characterized in that the gear ratio between the actuator gear element and the drive gear varies as they rotate during operation of the actuator.

12 Claims, 7 Drawing Sheets

(58) Field of Classification Search
CPC .......... A61M 15/0041; A61M 15/0043; A61M 15/0045; A61M 15/0055; A61M 15/0056; A61M 2202/064; F16H 2001/323; F16H 1/321
See application file for complete search history.

(56) References Cited

U.S. PATENT DOCUMENTS

| | | | | |
|---|---|---|---|---|
| 8,443,798 B2* | 5/2013 | Eason | ............... | A61M 15/0086 128/203.15 |
| 8,522,777 B2* | 9/2013 | Von Brunn | ....... | A61M 15/0055 128/200.14 |
| 2015/0174345 A1* | 6/2015 | Toksoz | .............. | A61M 15/0051 128/203.15 |

OTHER PUBLICATIONS

International Search Report from corresponding International Application No. PCT/EP2019/074978, mailed Dec. 4, 2019.
Written Opinion of the International Searching Authority issued on Dec. 4, 2019, from corresponding International Application No. PCT/EP2019/074978.

* cited by examiner

INHALER

TECHNICAL FIELD OF THE INVENTION

The present invention relates to a dry powder inhaler with a blister strip containing doses of one or more substances for inhalation. In particular, the invention relates to an inhaler having a mechanism for controlling the force that the user applies when actuating the inhaler.

BACKGROUND TO THE INVENTION

Inhalers provide an attractive method for administering medicaments, for example to treat local diseases of the airway or to deliver drugs to the bloodstream via the lungs. The medicament is commonly provided as a dry powder pre-packaged in individual doses, such as capsules or blisters. It is advantageous for the inhaler to hold a number of doses so that there is no need to insert a blister into the device each time it is used. Therefore, many inhalers include means for storing a number of doses, e.g. in the form of a blister strip. Such devices are disclosed in, for example, WO 05/037353 and WO 12/069854. These inhalers have an actuating lever which is rotated by the user in order to move the blister strip forwards and to pierce each blister so that the contents can be inhaled.

WO13/175176 discloses an inhaler of this type which has a mechanism for controlling the force that must be applied to the actuating lever to cause it to rotate throughout at least a substantial portion of the stroke of the actuating lever. The mechanism has a cantilever which runs up a ramp on the housing during rotation of the actuating lever. The ramp is shaped to change the degree of deflection of the cantilever, and hence the applied force, during the stroke of the actuating lever.

Whilst this mechanism allows the force to be controlled, it necessarily increases the applied force above that which is inherently required to index the blisters, at least initially. This is because deflection of the cantilever requires additional applied force. This could be disadvantageous in an inhaler which already requires a relatively high applied force; for example if the inhaler indexes and pierces more than one blister on each actuation, and/or or if the used blisters are squashed.

BRIEF DESCRIPTION OF THE INVENTION

The present invention provides an alternative way of controlling the force that the user applies to the actuator. The invention removes the need for the ramp and the cantilever by using non-circular gears.

Accordingly, the present invention provides an inhaler comprising:
- a housing which contains a blister strip having a plurality of blisters which contain powdered medicament for inhalation,
- a mouthpiece mounted on the housing through which the medicament is inhaled by a user,
- an actuator,
- a blister piercing member,
- an indexing wheel for sequentially moving each blister into alignment with the blister piercing member when the user operates the actuator,
- an actuator gear mounted for rotation about a first axis which is driven by the actuator, and which comprises an actuator gear element,
- a drive gear for driving the indexing wheel, mounted for rotation about a second axis, which engages with the actuator gear element,
characterised in that the gear ratio between the actuator gear element and the drive gear varies as they rotate during operation of the actuator.

The shapes of the gears are complementary so that the teeth on the actuator gear always engage with the teeth on the drive gear. In other words, the sum of the radius of the actuator gear and the radius of the drive gear is equal to the distance between their centres at every point during actuation. However, unlike circular gears, the radius of each gear, and hence the gear ratio, changes continually as the gears rotate. Consequently, the force applied by the user does not correspond to that required to index the blister strip and pierce the blisters. By designing the shape of the gears appropriately, the desired force profile can be obtained.

Preferably, the inhaler has an outer cover which is pivotally mounted on the housing. The outer cover may be passive, in the sense that it covers/uncovers the mouthpiece but does not have any other function.

In one embodiment, the actuator is formed as part of, or is connected to, the outer cover, so that rotation of the outer cover causes indexing of the blister strip and piercing of the blisters.

Alternatively, the inhaler has a lever which forms the actuator so that motion of the lever causes indexing of the blister strip and piercing of the blisters.

The actuator gear element preferably extends around part of the periphery of the actuator gear, although it may extend around the whole of the periphery of the actuator gear.

Preferably the gear ratio increases during a first part of actuation as the blister strip is indexed.

Preferably the gear ratio decreases during a second part of actuation as the blister strip is stationary and piercing takes place.

Preferably the blisters are squashed after they have been pierced.

In one embodiment, the inhaler indexes the blister strip by two blisters on each actuation. More preferably the gear ratio has a maximum at the region corresponding to the point in the actuation at which one blister of the two blisters has been squashed.

The invention also provides an inhaler comprising a housing which contains a blister strip having a plurality of blisters which contain powdered medicament for inhalation, a mouthpiece mounted on the housing through which the medicament is inhaled by a user, an outer cover which is mounted on the housing so that it pivots between a first, closed position in which the outer cover covers the mouthpiece, and a second, open position in which the mouthpiece is exposed, a blister piercing member, an indexing wheel for sequentially moving each blister into alignment with the blister piercing member, an actuator gear mounted for rotation about a first axis which is driven by the outer cover, and which comprises an actuator gear element, a drive gear for driving the indexing wheel, mounted for rotation about a second axis, which engages with the actuator gear element, wherein pivoting the outer cover from the closed position to the open position causes indexing and piercing of two blisters, characterized in that the gear ratio between the actuator gear element and the drive gear varies as they rotate during opening of the outer cover.

BRIEF DESCRIPTION OF THE FIGURES

The invention will now be further described with reference to the Figures, wherein.

DETAILED DESCRIPTION OF THE INVENTION

Figure 1A:
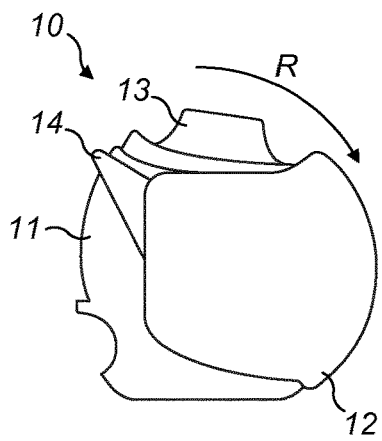
FIGS. 1A to 1E are a sequence of drawings to show the general function and operation of an inhaler of the type disclosed in WO 13/175176.

FIGS. 1A to 1E show the general function and operation of an inhaler of the type disclosed in WO 13/175176. The inhaler 10 has a housing 11 and a pivotally mounted outer cover 12. The outer cover 12 can be rotated through approximately 90° to expose a mouthpiece 13 and an actuating lever 14. Inside the housing in the underside of the mouthpiece is a piercer (not visible in FIG. 1). The inhaler is operated as follows.

Figure 1B:
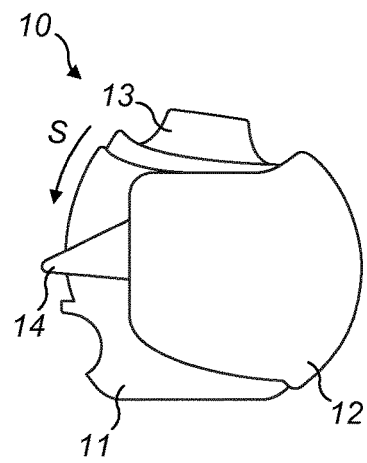

The cover 12 is rotated into its fully open position in the direction of arrow "R" as indicated in FIG. 1A. The user then applies pressure to the actuating lever 14, so that it rotates in the direction indicated by arrow "S" in FIG. 1B. During initial rotation of the actuating lever 14 through a first portion of its stroke into the position as it is shown in FIG. 1B, the actuating lever drives a blister strip indexing wheel by a mechanism which is described below. The indexing wheel indexes the blister strip so as to move an unused blister into alignment with the piercer.

Figure 1C:
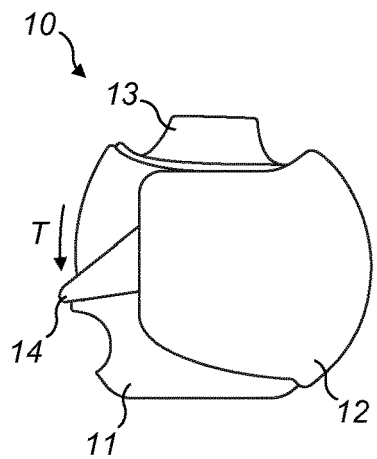
Figure 1D:
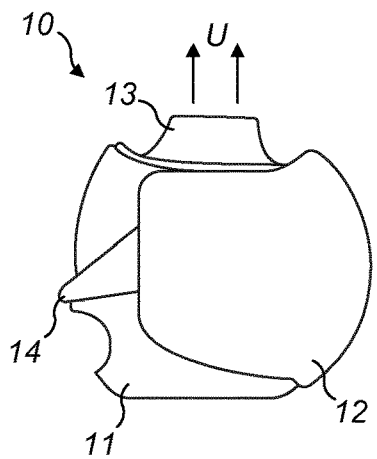
Figure 1E:
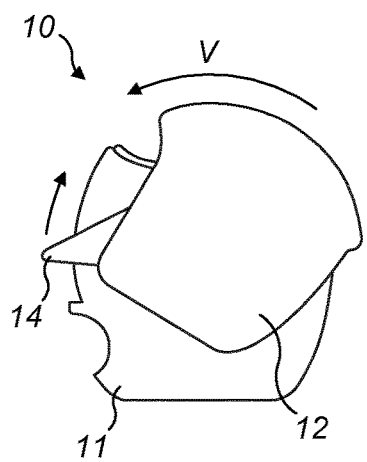

When the actuating member is rotated through a second portion of its stroke as indicated by arrow "T" in FIG. 1C, the blister strip remains stationary but the mouthpiece 13 is now pivoted so that the piercer pierces the lid of the aligned blister. The user then inhales through the mouthpiece 13, as shown by arrows "U" in FIG. 1D.

After inhalation, the user rotates the cover 12 in the opposite direction, as indicated by "V" in FIG. 3(e). During this movement, the cover 12 engages with the actuating lever 14 so that the actuating lever 14 also returns to the initial position of FIG. 1A. The blister strip remains stationary during this return movement of the actuating lever 14.

Figure 2A:
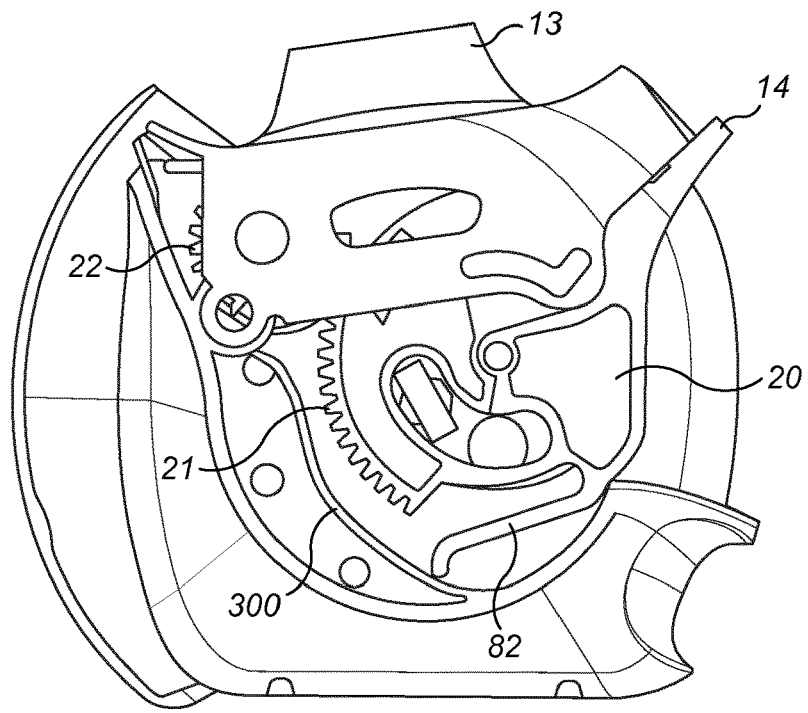
FIGS. 2A and 2B show the inhaler of WO 13/175176 with the outer cover removed so that the internal components are visible.
Figure 2B:
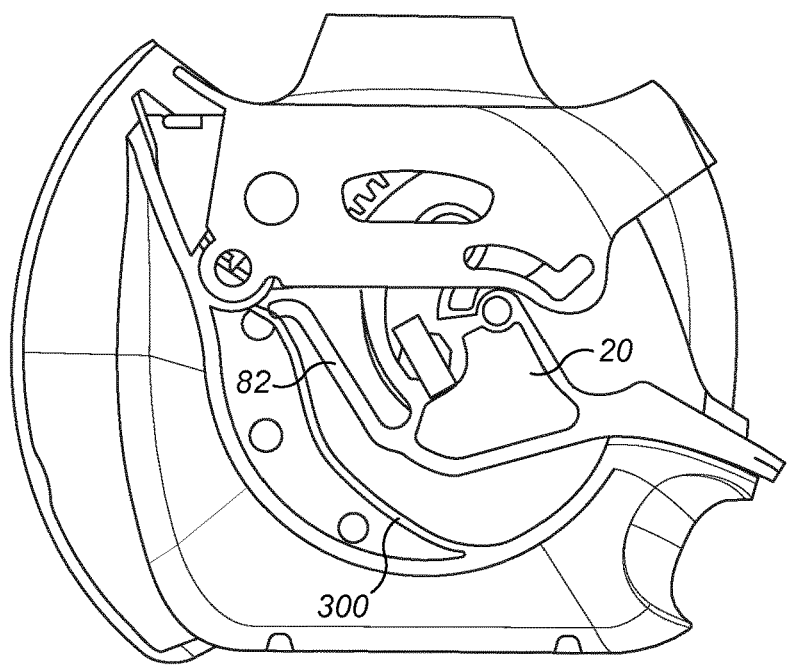
Figure 2C:
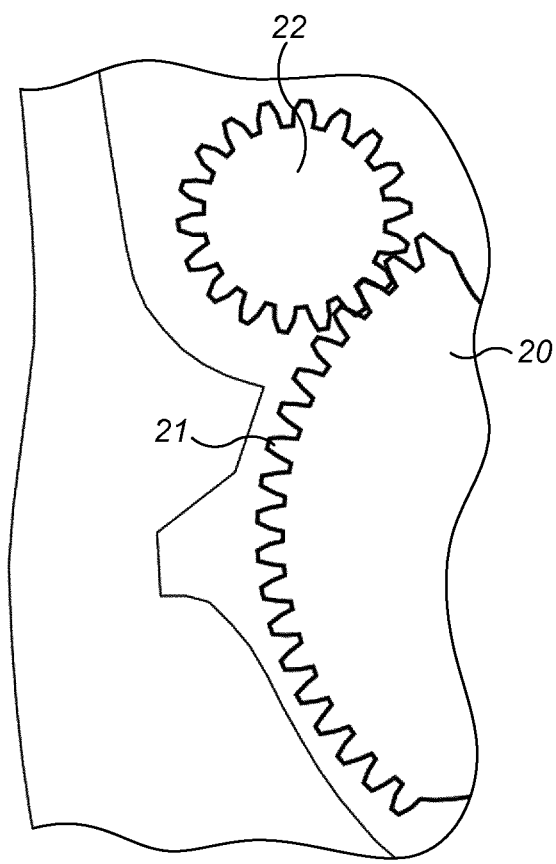
FIG. 2C shows the actuator gear and drive gear.

FIG. 2 shows the inhaler of WO 13/175176 with one side of the cover removed so that the actuation mechanism can be seen. FIG. 2 is a view from the opposite side of the inhaler from FIG. 1, so that the actuating lever is on the right side of the device. In FIG. 2A, the actuating lever is in its initial position. In FIG. 2B the actuating lever has been fully rotated. The actuating lever 14 is formed as part of a pivotally mounted actuator gear 20. An actuator gear element 21 is located on the opposite side of the actuator gear 20 from the actuating lever 14. The gear element 21 is formed by gear teeth which extend in a circular arc around part of the circumference of the actuator gear 20. The gear element 21 engages with a drive gear wheel 22 which is selectively coupled to and uncoupled from the blister strip indexing wheel by a drive coupling (not shown). In FIGS. 2A and 2B, the drive gear wheel 22 is largely hidden behind the bottom part of the mouthpiece 13. FIG. 2C is a close-up view with the mouthpiece 13 removed so that the drive gear wheel 22 and actuator gear element 21 are visible.

As the user rotates the actuating lever through the first portion of its stroke (arrow S in FIG. 1B), the gear element 21 causes the drive gear 22 and drive coupling to rotate. At this point, the drive coupling is engaged with the indexing wheel so the indexing wheel also rotates, and thereby moves the unused blister into alignment with the piercer. At the same time, the previously used blister is squashed between the indexing wheel and the inner surface of the housing, in order to reduce the amount of space that is occupied by the used blister strip. Further rotating the actuating lever 14 causes the drive coupling to disengage from the indexing wheel so that the blister strip is stationary while the piercer pierces the lid of the aligned blister. The user then inhales through the mouthpiece, which generates an airflow through the opened blister to entrain the medicament and carry it into the user's airway.

The operation of the drive coupling, indexing wheel and piercer to perform indexing, piercing and squashing of the blisters is described in WO 13/175176 and is not repeated here. WO 13/175176 also discloses a variant in which the outer cover causes actuation instead of the actuating lever. The actuator gear is connected to, or formed as part of, the outer cover, so that opening the cover not only exposes the mouthpiece, but also indexes and pierces the blisters.

The inhaler of WO 13/175176 includes a mechanism for controlling the force that must be applied to the actuating lever in order to actuate the inhaler, shown in FIGS. 2A and 2B. The actuator gear 20 has a cantilever 82 which runs up a corresponding ramp 300 on the housing during rotation of the actuating lever from its initial position to its fully depressed position so that a biasing force is applied to the cantilever 82 during the stroke of the actuating lever 14. The ramp deflects the cantilever and the resilience of the deflected cantilever applies a biasing force to the actuator that must be overcome by the user. The deflection of the cantilever 82, and hence the biasing force, is determined by the shape of the ramp. For example, the ramp 300 may be shaped so that the biasing force is relatively high during rotation of the actuating lever 14 until just before the blister is pierced, and then decreases beyond this point, thereby guiding the user to complete the actuation stroke and pierce the blister.

This mechanism allows the force to be controlled. However, it necessarily increases the applied force above that which is inherently required to index the blisters, at least initially. This is because deflection of the cantilever requires additional applied force. This can be disadvantageous in an inhaler which already requires a relatively high applied force; for example if the inhaler indexes and pierces more than one blister on each actuation, and/or or if the used blisters must be squashed completely. The stored energy resulting from deflection of the cantilever can be subsequently released, for example at the end of actuation in order to pull the actuator to the end of the stroke. However, there is no possibility of reducing the force that must be applied at the start of actuation.

The present invention provides an alternative mechanism for controlling the applied force, which has the additional advantage that the force can be decreased in the initial part of the actuator stroke. This is achieved by the actuator gear and drive gear being non-circular, so that the gear ratio is not a constant, but instead varies with the angular position of the actuator.

Figure 3A:
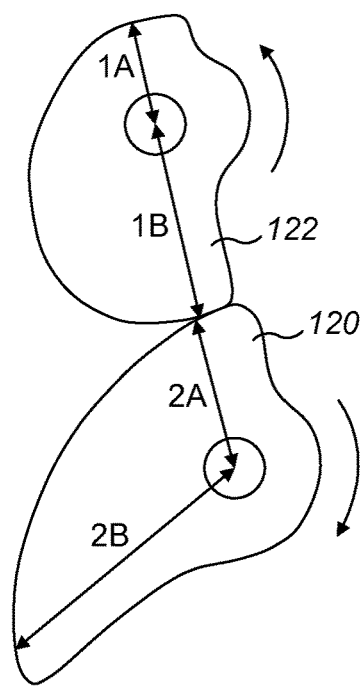
FIG. 3A schematically shows non-circular actuator and drive gears in accordance with the invention.
Figure 3B:
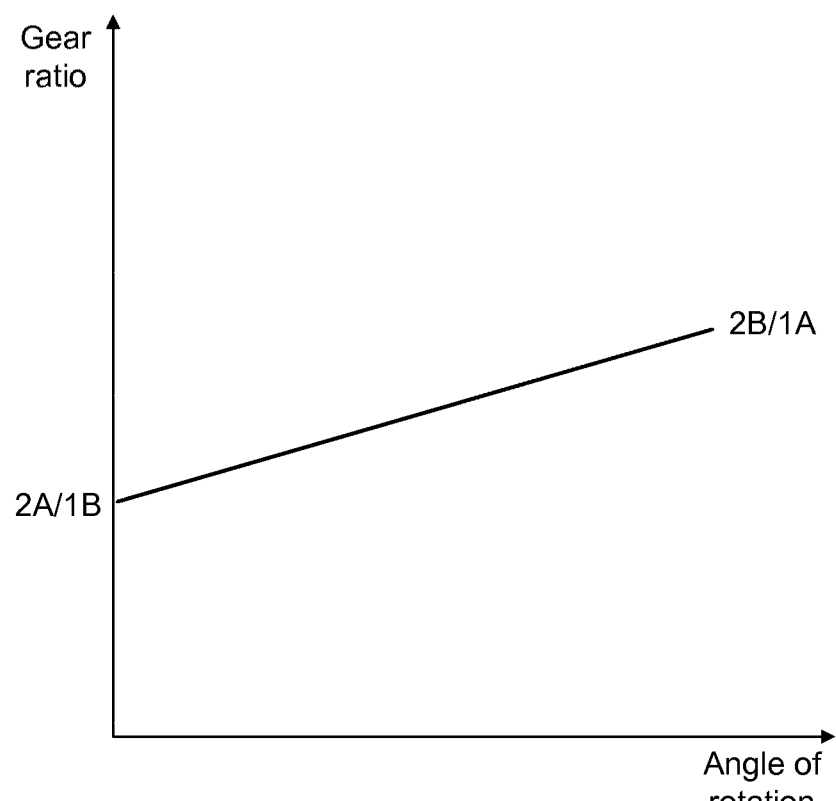
FIG. 3B shows the corresponding gear ratio as a function of angular position.

FIG. 3A is a schematic diagram showing a non-circular actuator gear 120 and drive gear 122 in accordance with the invention. The distance between their axes is fixed, and the shapes of the gears are designed so that they always mesh along the line joining the axes. In this case, the radius of the actuator gear increases steadily from a small value (2A) when the actuator is in its initial position to a larger value (2B) when the actuator is in its fully actuated positon, when it has rotated through approximately 120°. Correspondingly, the radius of the drive gear decreases from a large value (1B) to a small value (1A) through the actuation stroke when it has rotated through approximately 180°. The sum of the radius of the actuator gear and the drive gear at the point at which they mesh is constant, i.e. 2A+1B=2B+1A, while the gear ratio increases continually from 2A/1B to 2B/1A, as shown in FIG. 3B (whereas if the gears were circular, the gear ratio would be constant). Consequently, the force that the user must apply increases during the actuation stroke.

Figure 4A:
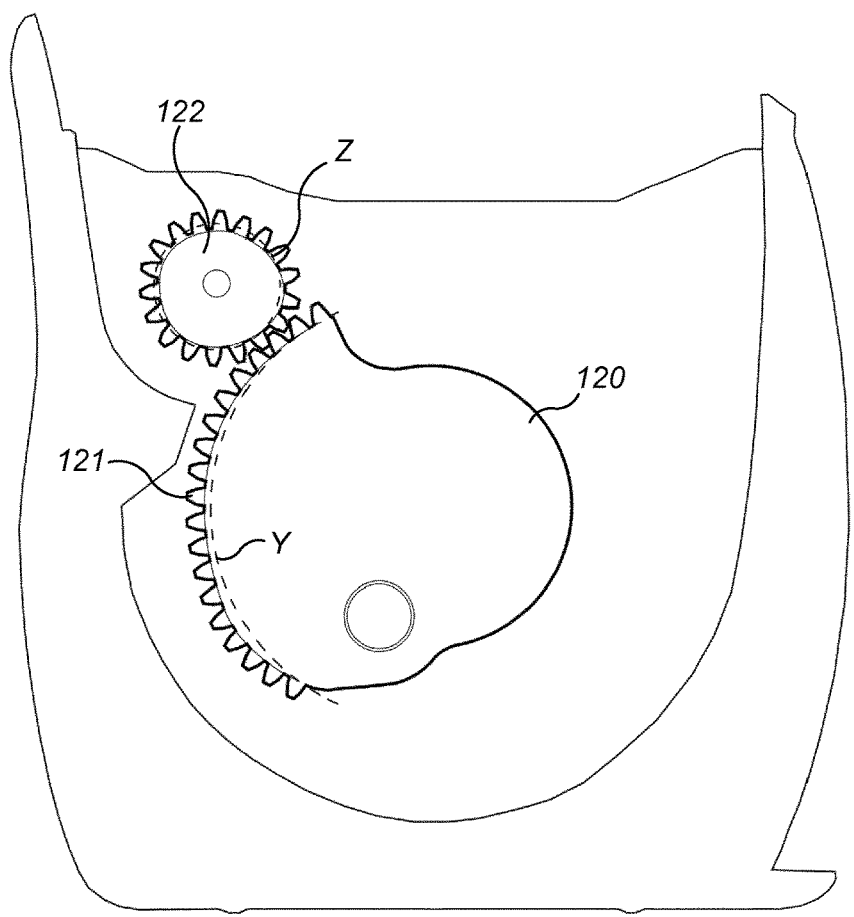
FIG. 4A shows the gear mechanism of an inhaler according to the invention in which the force profile of WO 13/175176 is replicated using non-circular gears.

FIG. 4A schematically shows an inhaler in which the force profile of WO 13/175176 is replicated using non-circular gears. The dashed line Y is an arc which corresponds to the base of the gear teeth in the circular actuator gear element of WO 13/175176. The gears are shown in the initial (not yet actuated) position.

The non-circular actuator gear element 121 deviates from the circular arc. The radius of the gear element gradually increases along the gear element in an anticlockwise direction and reaches its maximum value approximately three quarters of the way around. The radius then decreases relatively rapidly. In a corresponding manner, drive gear 122 deviates from the dashed line Z which represents the drive gear of WO 13/175176. The radius of the drive gear 122 decreases from the point at which the gears are in contact in FIG. 4A, so that the base of the teeth lie inside the dashed line Z.

Figure 4B:
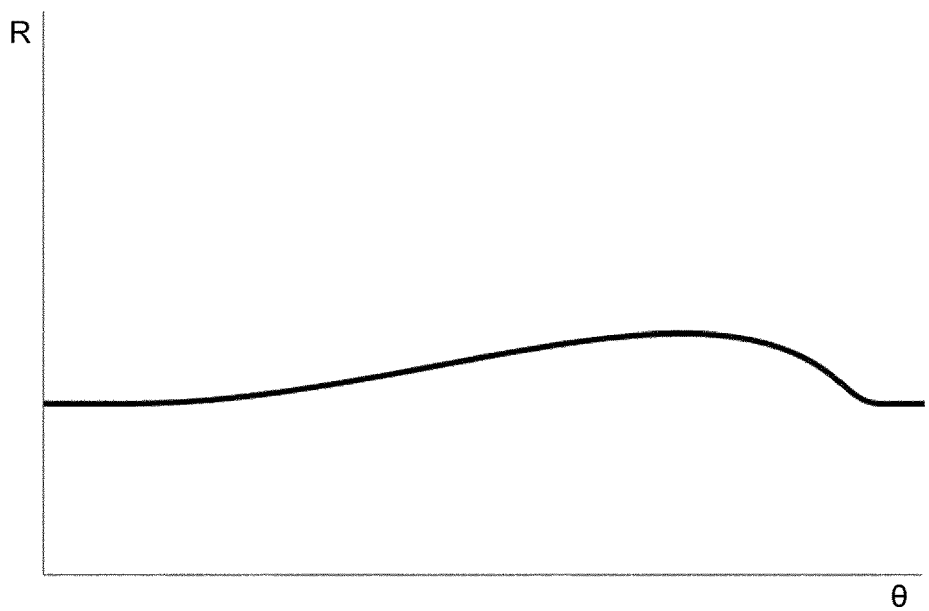
FIG. 4B shows the corresponding gear ratio as a function of angular position.

FIG. 4B shows the resulting gear ratio R (given by the radius of the actuator gear element divided by the radius of the drive gear) as a function of angular position θ of the gears. The gear ratio, and hence the force that must be applied by the user, increases gradually to a maximum corresponding to a point just before the blister is pierced. The gear ratio then decreases, thereby guiding the user to complete the actuation stroke and pierce the blister.

In the treatment of respiratory disorders it is often beneficial to administer a combination of active pharmaceutical ingredients (APIs) to a patient, for example a bronchodilator and an anti-inflammatory drug, such as salmeterol and fluticasone, or a triple combination such as a long acting β2-agonist (LABA), a long-acting muscarinic antagonist (LAMA) and a corticosteroid. However, the APIs typically have very different physicochemical properties; this affects, for example, their interactions with carrier particles. Consequently, it is very difficult to co-formulate two or three APIs in a single powder with the desired aerosolization properties.

One way to circumvent this problem is separate the APIs. WO 09/092520 discloses an inhaler in which the blister strip is moved onwards by two blister pockets (one containing each formulation) in each indexing operation. The inhaler has two piercing elements for simultaneously piercing the blister pockets aligned with each piercing element.

One way of indexing the blister strip by two blisters on each actuation would be to increase (approximately double) the angle through which the actuator pivots. In a conventional device, the actuator typically is pivoted through about 90°. However, increasing this to about 180° would make the device less easy to use. The extra angular motion of the actuator would be more difficult to achieve with one hand, and also moving the actuator through a much larger angle would restrict where the user could hold the main body of the device with the other hand during actuation. An alternative approach would be to increase (approximately double) the gear ratio between the actuator and the indexing wheel, so that the same pivot angle moves the blister strip twice as far. However, the force required to operate the actuator is correspondingly increased, which could make the inhaler harder to operate, especially for elderly or infirm patients, or for young children.

Moreover, it is advantageous for the used blisters to be squashed or crushed after they have been emptied, so that the used portion of the blister strip takes up less space. This can be achieved, for example, by positioning the indexing wheel such that the distance between the hub of the wheel and the inner surface of the housing is less than the depth of a blister. In this way, onward rotation of the indexing wheel after piercing causes each blister to be at least partially squashed between the hub and the wall. This increases the force that must be applied to the actuator during indexing.

Figure 5A:
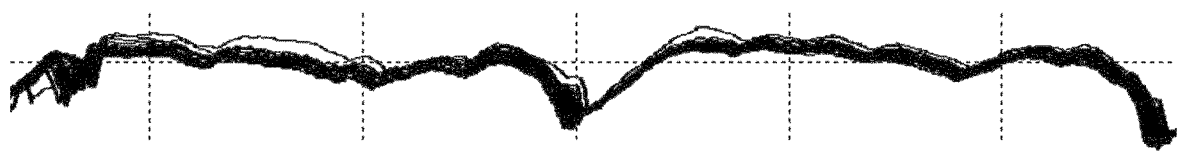
FIG. 5A shows the applied force as a function of the angular position of the actuator for an inhaler which indexes two blisters in each actuation.

FIG. 5A shows the applied force as a function of the angular position of the actuator for an inhaler which indexes two blisters in each actuation. There are two regions where the force is high, corresponding to the stages at which the each empty blister is crushed, with a reduction in the applied force between them. The user could feel this reduction and mistakenly think that this indicates that actuation is complete. If they then inhaled, they would not receive any powder since the blisters have not been fully indexed and pierced. This can be addressed by shaping the actuator gear and drive gear so that there is a peak in the gear ratio corresponding to the gap between the two blisters.

Figure 5B:
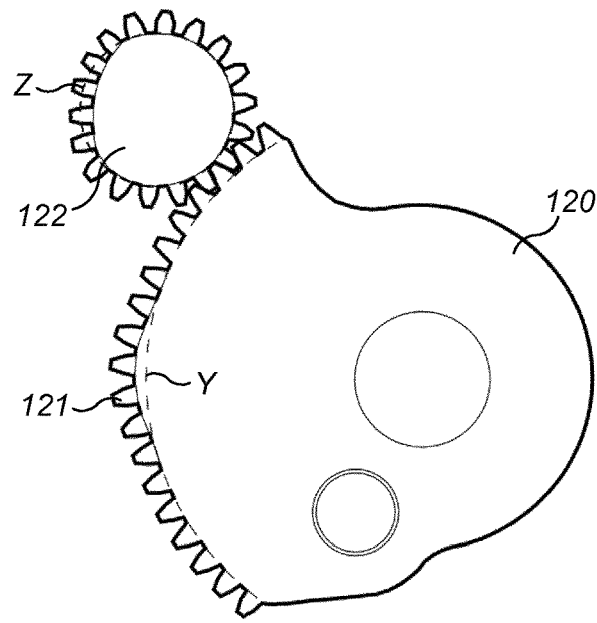
FIG. 5B shows the gear mechanism of an inhaler according to the invention, which indexes and pierces two blister on each actuation.
Figure 5C:
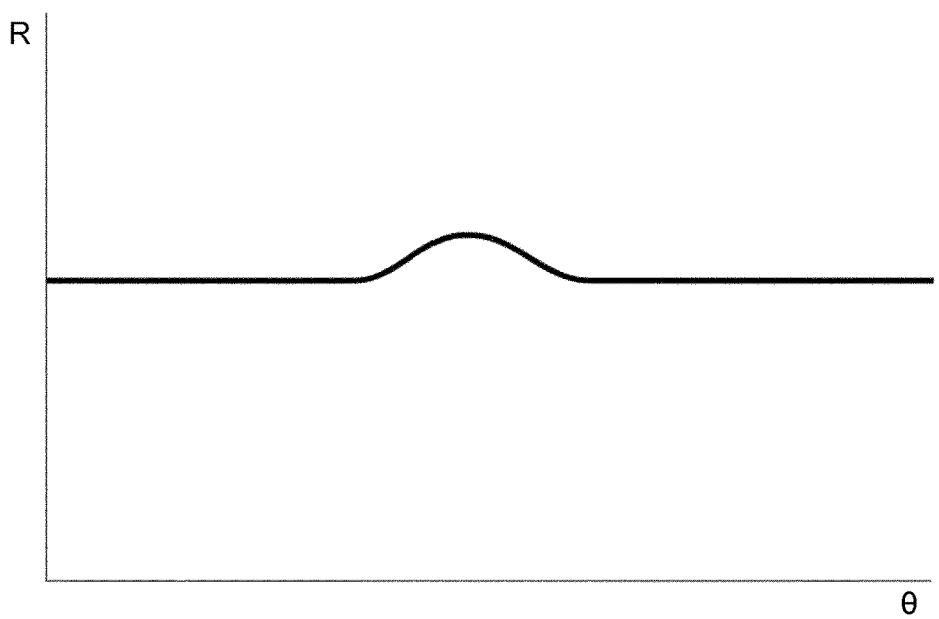
FIG. 5C shows the corresponding gear ratio as a function of angular position.

FIG. 5B shows an actuator gear 120 and a drive gear 122 in accordance with the invention that produce a peak in the force midway through the stroke of the actuator. The actuator gear element 121 has a bump at its centre where the radius is larger than the circular arc Y. Similarly, the drive gear is flattened so that it lies inside the dashed circle Z in the corresponding region. As shown in FIG. 5C, this results in an increased gear ratio in this region. Consequently, the force that the user must apply is increased, thereby masking the reduction in the applied force that would otherwise occur between crushing of the two blisters.

The gears can be of course designed to produce gear ratios that vary in many different ways. For example, in addition to compensating for the reduction, the gears could be arranged to smooth out the peaks in the inherently required force and thereby spread the work more evenly over the angular motion of the actuator. For example, the profile of FIG. 5C could be modified so that there is a decrease in the gear ratio in the regions corresponding to the highest values of the applied force in FIG. 5A. Similarly, the profiles of FIG. 4B and FIG. 5C could be combined to result in an applied force which gradually increases from the start of actuation in a steady manner up to the point at which piercing occurs whilst also compensating for the reduction in required force between squashing two blisters.

Figure 6:
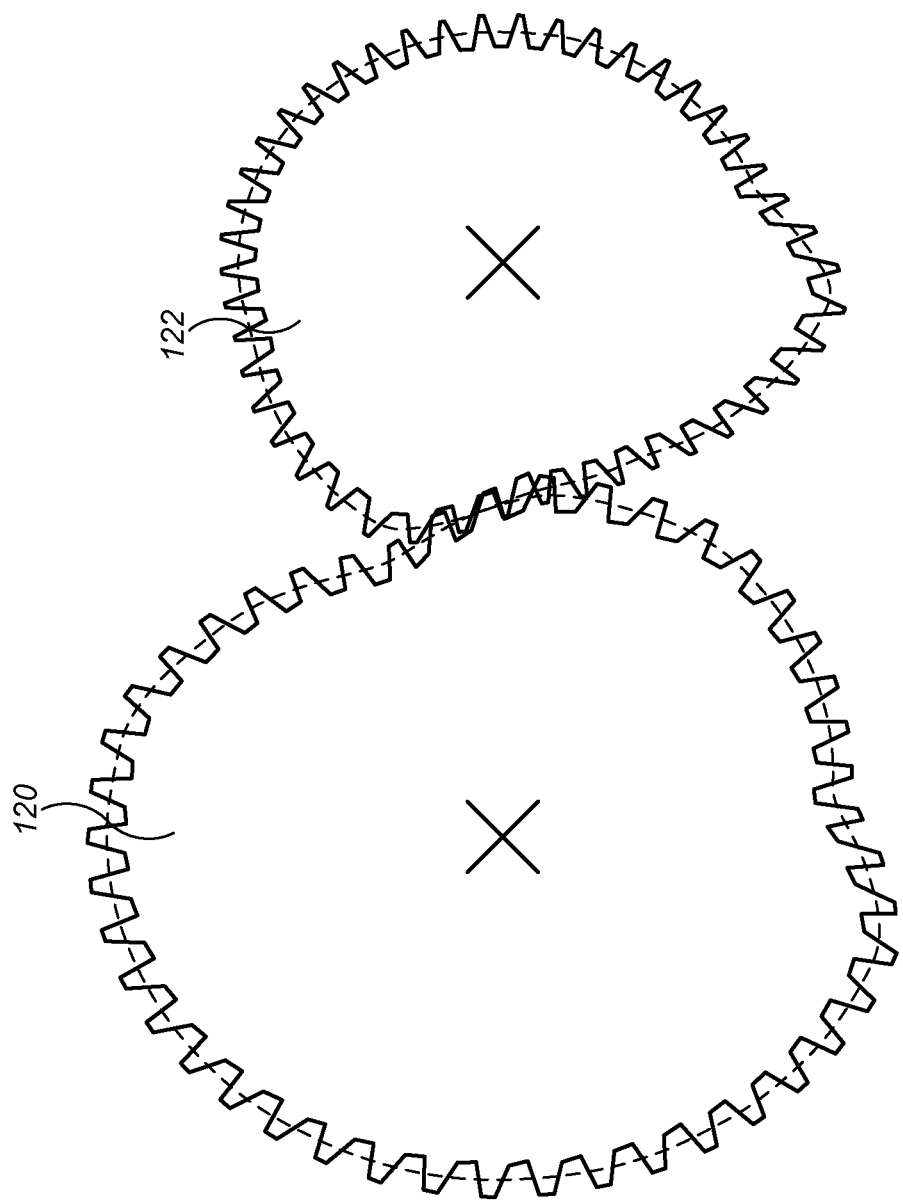
FIG. 6 shows a further gear mechanism in accordance with the invention, in which the actuator gear takes the form of a full gear wheel.

The actuator gears shown in FIGS. 3, 4 and 5 have gear elements around part of their length. However, the invention can equally be applied to an actuator gear 120 which takes the form of a full gear wheel with teeth around the whole of its periphery, as shown in FIG. 6, together with the corresponding drive gear 122.

The invention claimed is:

1. An inhaler comprising:
    a housing which contains a blister strip having a plurality of blisters which contain powdered medicament for inhalation,
    a mouthpiece mounted on the housing through which the medicament is inhaled by a user,
    an actuator,
    a blister piercing member,
    an indexing wheel for sequentially moving each blister into alignment with the blister piercing member when the user operates the actuator,
    an actuator gear, mounted for rotation about a first axis, which is driven by the actuator and which comprises an actuator gear element,
    a drive gear for driving the indexing wheel, mounted for rotation about a second axis, which engages with the actuator gear element,
    characterized in that the gear ratio between the actuator gear element and the drive gear varies as they rotate during operation of the actuator.

2. An inhaler according to claim 1, wherein the inhaler has an outer cover which is pivotally mounted on the housing.

3. An inhaler according to claim 2, wherein the actuator is formed as part of, or is connected to, the outer cover, so that rotation of the outer cover causes indexing of the blister strip and piercing of the blisters.

4. An inhaler according to claim 1, wherein the inhaler has a lever which forms the actuator so that motion of the lever causes indexing of the blister strip and piercing of the blisters.

5. An inhaler according to claim 1, wherein the actuator gear element extends around part of the periphery of the actuator gear.

6. An inhaler according to claim 1, wherein the actuator gear element extends around the whole of the periphery of the actuator gear.

7. An inhaler according to claim 1, wherein the gear ratio increases during a first part of actuation as the blister strip is indexed.

8. An inhaler according to claim 7, wherein the gear ratio decreases during a second part of actuation as the blister strip is stationary and piercing takes place.

9. An inhaler according to claim 1, which indexes the blister strip by two blisters on each actuation.

10. An inhaler according to claim 9, wherein the blisters are squashed after they have been pierced.

11. An inhaler according to claim 10, wherein the gear ratio has a maximum at the region corresponding to a point in the actuation at which one blister of the two blisters has been squashed.

12. An inhaler comprising a housing which contains a blister strip having a plurality of blisters which contain powdered medicament for inhalation, a mouthpiece mounted on the housing through which the medicament is inhaled by a user, an outer cover which is mounted on the housing so that it pivots between a first, closed position in which the outer cover covers the mouthpiece, and a second, open position in which the mouthpiece is exposed, a blister piercing member, an indexing wheel for sequentially moving each blister into alignment with the blister piercing member, an actuator gear mounted for rotation about a first axis which is driven by the outer cover, and which comprises an actuator gear element, a drive gear for driving the indexing wheel, mounted for rotation about a second axis, which engages with the actuator gear element, wherein pivoting the outer cover from the closed position to the open position causes indexing and piercing of two blisters, characterized in that the gear ratio between the actuator gear element and the drive gear varies as they rotate during opening of the outer cover.

* * * * *